(12) United States Patent  (10) Patent No.: US 6,471,702 B1
Goto  (45) Date of Patent: Oct. 29, 2002

(54) ENDOSCOPIC HIGH-FREQUENCY KNIFE

(76) Inventor: Hiroaki Goto, c/o Intellectual Property Department, Olympus Optical Co., Ltd., 2-3, Kuboyama-cho, Hachioji-shi, Tokyo (JP)

( * ) Notice: Subject to any disclaimer, the term of this patent is extended or adjusted under 35 U.S.C. 154(b) by 138 days.

(21) Appl. No.: 09/610,295

(22) Filed: Jul. 5, 2000

(30) Foreign Application Priority Data

Jul. 8, 1999 (JP) ............................................. 11-194459
Jun. 2, 2000 (JP) ........................................ 2000-166195

(51) Int. Cl.[7] ............................................... A61B 18/18
(52) U.S. Cl. ........................................... 606/47; 606/46
(58) Field of Search .............................. 606/41, 45, 46, 606/47

(56) References Cited

U.S. PATENT DOCUMENTS

| | | | | |
|---|---|---|---|---|
| 3,910,279 A | * | 10/1975 | Okada et al. | 606/47 |
| 5,163,938 A | * | 11/1992 | Kambara et al. | 606/47 |
| 5,984,920 A | * | 11/1999 | Steinbach | 606/47 |
| 6,017,339 A | | 1/2000 | Sadamasa | |

FOREIGN PATENT DOCUMENTS

| | | |
|---|---|---|
| DE | 197 03 860 A1 | 8/1997 |
| JP | 4-364836 | * 12/1992 |
| JP | 5-176940 | 7/1993 |
| JP | 09-285472 | 11/1997 |

OTHER PUBLICATIONS

German Official Action, Mailing Date—Jul. 13, 2001, issued by the German Patent Office in counterpart German Application Serial No. 100 32 766.4–35.

* cited by examiner

Primary Examiner—Michael Peffley
(74) Attorney, Agent, or Firm—Frishauf, Holtz, Goodman & Chick, P.C.

(57) ABSTRACT

An endoscopic high-frequency knife is provided in which, on the external wall of a sheath, two grooves for exposing a knife wire to the external wall surface are formed along the longitudinal axis and are punched to be spaced from each other. In addition, a knife chip fixed along the longitudinal axis of the sheath is provided at the tip end portion of the knife wire. The knife wire has a guide arm section formed by bending a portion adjacent to the knife chip. The guide arm section is disposed at the tip end groove. The tip end of an exposed portion exposed to the external wall side is overhung laterally of the sheath longitudinal central plane passing through the two grooves and the knife chip.

10 Claims, 4 Drawing Sheets

ENDOSCOPIC HIGH-FREQUENCY KNIFE

CROSS-REFERENCE TO RELATED APPLICATIONS

This application is based upon and claims the benefit of priority from the prior Japanese Patent Applications No. 11-194459, filed Jul. 8, 1999; and No. 2000-166195, filed Jun. 2, 2000, the entire contents of which are incorporated herein by reference.

BACKGROUND OF THE INVENTION

The present invention relates to an endoscopic high-frequency knife. Such a high-frequency knife is typically inserted trans-endoscopically into a body for dissecting tissues such as duodenal papilla.

Conventionally, a high-frequency knife for dissecting a diseased portion in a cavity by using a high-frequency current has been known. An example of such high-frequency knife is disclosed in Jpn. Pat. Appln. KOKAI Publication No. 9-285472, Jpn. Pat. Appln. KOKAI Publication No. 4-364836, and Jpn. Pat. Appln. KOKAI Publication No. 5-176940 or the like, for example. Generally, such a high-frequency knife has a conductive wire inserted in a flexible sheath, and this wire is exposed to an external wall surface at a tip end portion of the sheath. When a surgeon pulls the wire, the tip end portion of the sheath is bent, whereby an exposed wire portion is tensioned, and a dissection portion is formed. When this dissection portion is brought into contact with a diseased portion, a high-frequency current is supplied to the wire, whereby the diseased portion can be dissected.

Generally, such a high-frequency knife disposes a dissection portion according to a state of the diseased portion in a cavity, resulting in a complicated structure. For example, in the duodenum, in the case where an exit of a bile duct carrying bile to the duodenum is narrowed by a tumor or stone and the like, it is known that a papilla sphincterectomy (hereinafter, referred to as EST) for dissecting a sphincter that is present at a distal end of the bile duct is performed. In this EST, since the pancreas is positioned on the right side of a site to be dissected, it is desirable that the dissection portion of the conductive wire of the high-frequency knife be positioned at the left side opposite to the pancreas when the sheath tip end is seen from the proximal end.

When using the conventional high-frequency knife, the following undesirable situation very often occurs. That is, in the case of the high-frequency knife described in Jpn. Pat. Appln. KOKAI Publication No. 9-285472 that is the above prior art, a direction control plate for controlling an orientation of the knife extends from a tip end portion of the sheath to the vicinity of the proximal end thereof, and a relative rotation along a longitudinal axis between this direction control plate and the sheath is restricted, whereby the tip end can be easily rotated from the proximal end of the sheath. However, in this high-frequency knife, its configuration and operation become complicated. As for the configuration, the number of parts is increased, and the assembling process becomes complicated because the direction control plate and means for restricting this rotation are required, whereby parts cost and assembling cost are increased. As for the operation, a complicated operation for rotating a dissection portion of this high-frequency knife to a predetermined position after the high-frequency knife has been inserted into the nipple portion must be performed.

In addition, in the high-frequency knife disclosed in Jpn. Pat. Appln. KOKAI Publication No. 4-364836, a complicated direction control means for restricting a curved direction is provided at the sheath. Further, in the high-frequency knife described in Jpn. Pat. Appln. KOKAI Publication No. 5-176940, there are provided a plurality of wires for restricting a curved direction, whereby the number of parts is increased, and the assembling process becomes complicated. Therefore, in these high-frequency knives, there will occur a problem similar to the aforementioned problem that parts cost and assembling cost are increased.

BRIEF SUMMARY OF THE INVENTION

The present invention has been made in view of the foregoing circumstance. It is an object of the present invention to provide a high-frequency knife which has an extremely simple structure and which is capable of reliably orienting a dissection portion in a desired direction.

In order to achieve the foregoing object, according to the present invention, there is provided an endoscopic high-frequency knife comprising: a flexible sheath inserted into a body; and a conductive wire inserted into the sheath; wherein the sheath has a tip end portion at which a part of the wire is exposed to an external wall surface; wherein the tip end portion is bended by pulling and pushing the wire; and wherein an exposed wire portion is tensioned, thereby forming a dissection portion. This high-frequency knife comprises: two grooves which are punched at the external wall of the sheath along a longitudinal axis and to be spaced each other, the grooves causing the wire to be exposed to the external wall surface; a sheath longitudinal central plane which passes through the two grooves and a fixing section which is provided at the tip end portion of the wire and fixed along the longitudinal axis of the sheath; and a guide arm section formed by bending a portion adjacent to the fixing section. The guide arm section is disposed at a tip end groove of the two grooves, and the wire portion exposed to the external wall surface is overhung laterally of the longitudinal central plane at the tip end of the wire portion.

Thus, according to the present invention, an endoscopic high-frequency knife which has an extremely simple structure and which is capable of reliably orienting a dissection portion in a desired direction can be obtained. Further, the structure of the guide arm section both makes it difficult to slip off a knife wire from the sheath, and. makes it possible to smoothly dissect the desired site.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE INVENTION

Hereinafter, preferred embodiments of the present invention will be described in detail with reference to the accompanying drawings. In these drawings, FIG. 1A to FIG. 5B show a first embodiment of the present invention.

Figure 1A:
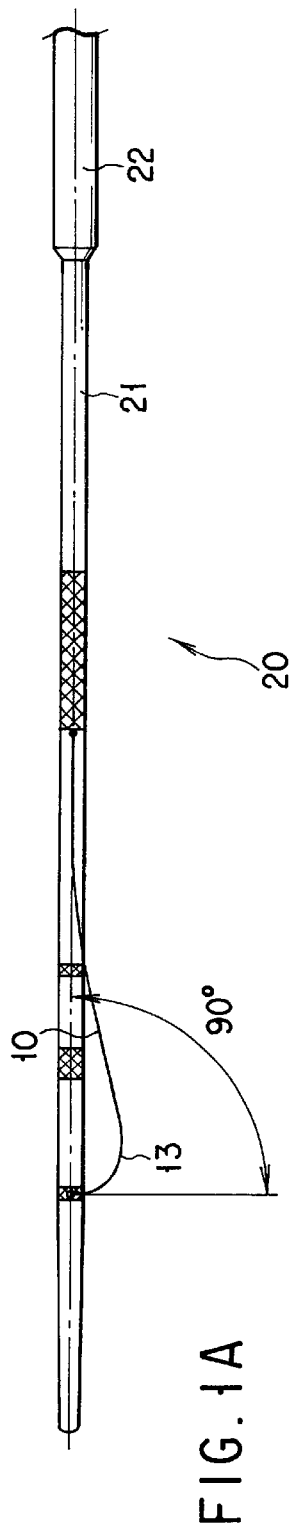
FIG. 1A is a schematic view showing a frontal side of a high-frequency knife according to a first embodiment of the present invention.
Figure 1B:
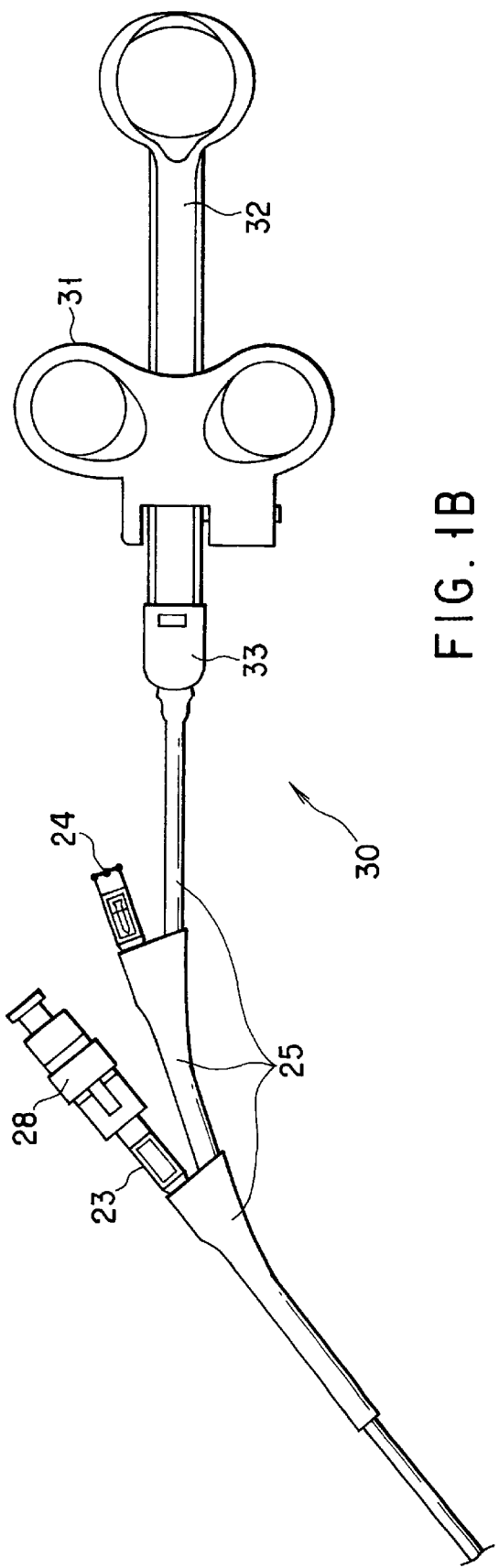
FIG. 1B is an enlarged view showing a tip end thereof.

As its appearance is schematically shown in FIG. 1A and FIG. 1B, a high-frequency knife in the first embodiment can be preferably employed for EST in particular, and comprises a knife wire 10, a sheath 20, and an operating section 30 as essential constituent members. The knife wire 10 is inserted into the sheath 20 and forms an insert section capable of being inserted into cavities, for example transendoscopically, together with the sheath 20. The tip end can be bent in a predetermined direction by extra-corporeal operation using an operating section 30 disposed on the proximal side.

Figure 2:
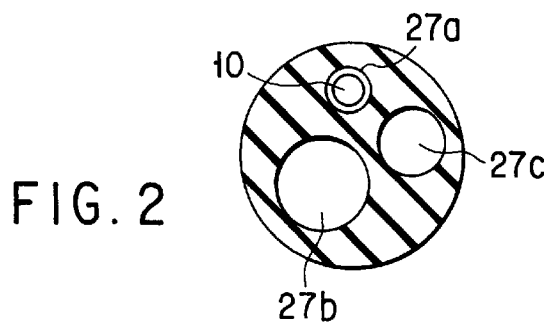
FIG. 2 is a transverse cross section showing a sheath in the high-frequency shown in FIGS. 1A and 1B.
Figure 3:
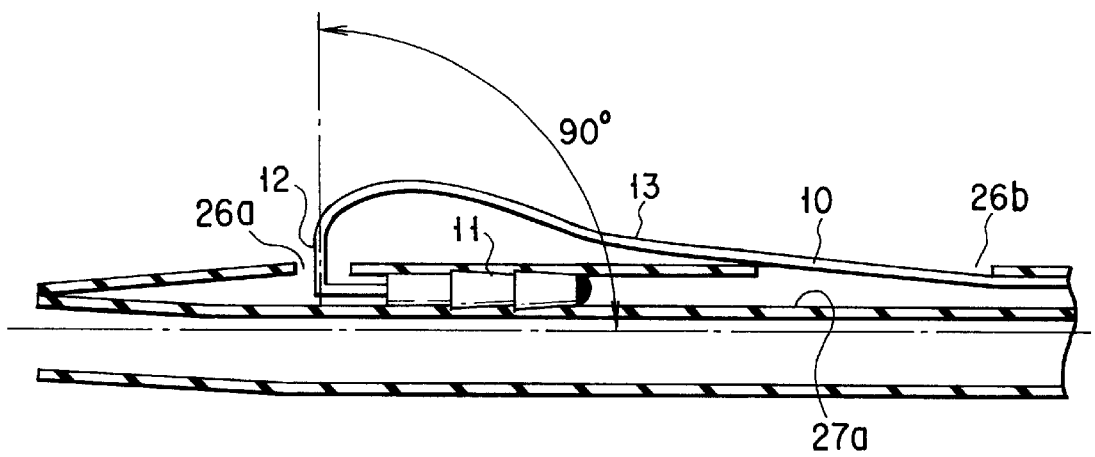
FIG. 3 is a longitudinal cross section showing a sheath tip end in the high-frequency knife shown in FIGS. 1A and 1B.
Figure 4:
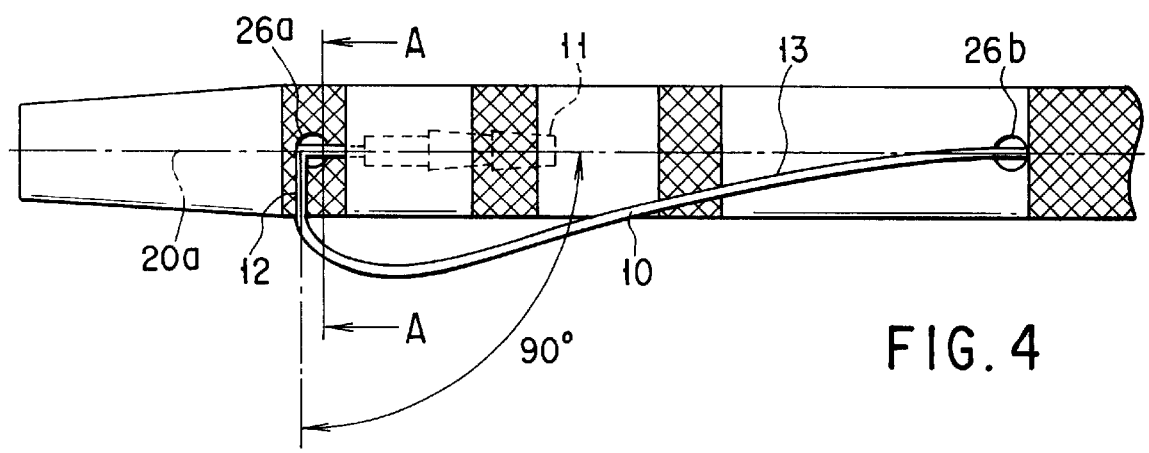
FIG. 4 is an illustrative view showing a top view of the sheath tip end portion shown in FIG. 3.

In FIG. 2, as the transverse cross section of the sheath 20 is schematically shown, the sheath 20 in the present embodiment is formed of a preferred material having electrical insulation properties and flexibility. The sheath is formed as a multi-lumen tube having three lumens 27a, 27b, and 27c along the longitudinal axis extended therein. In this sheath 20, the outer diameter of a tip end portion 21 is formed to have a smaller diameter than a proximal end portion 22, and its external wall surface is formed on a smooth cylindrical face. In addition, at the tip end portion 21 of this sheath 20, as shown in FIG. 3 and FIG. 4, two circular hole shaped grooves (i.e., slits) 26a and 26b extending through the external wall are spaced from each other along the longitudinal axis. Via these grooves 26a and 26b, a lumen 27a with its smallest diameter communicates with the external wall surface.

Further, as the enlarged cross section of a tip end portion of the sheath along the longitudinal direction is shown in FIG. 3, a knife chip 11 that is a fixing section for fixing this knife wire 10 to the sheath 20 is connected to the tip end of the knife wire 10 in the present embodiment. This knife chip 11 is fixed in the lumen 27a with the smallest diameter, while its tip end is oriented on the proximal end of the sheath 20. The fixing section fixed in this lumen 27a, i.e., a knife chip 11 may have a proper detent for preventing movement of the sheath 20 to the tip end. Although this knife chip 11 is fixed to the lumen 27a having the smallest diameter, for example, in the present embodiment, the knife chip is not limited thereto. As has been described above, any one of the three lumens 27a, 27b, and 27c of the sheath 20 may be employed if it communicates with a groove that opens on the external wall surface as described above.

In addition, the knife wire 10 of the present embodiment has a guide arm section 12 bent by about 90 degrees with respect to the axis of the knife chip 11 at an adjacent portion of the proximal end of the knife chip 11. This guide arm section 12 causes the lumen 27a as described above to be disposed in a tip end groove 26a of two grooves 26a and 26b which communicate with the external wall surface. In this manner, this knife wire 10 returns into the lumen 27a via the proximal end groove 26b after a portion adjacent to the guide arm section 12 has been exposed to the external wall surface of the sheath 20, thereby forming the exposed portion 13 as described above.

The proximal end portion of the knife wire 10 is extended to the operating section 30 through the lumen 27a, is connected to a slider 31 capable of sliding on a main body part 32 of the operating section 30, and is connected to a high-frequency power source (not shown) via this operating section 30. In addition, the other two lumens 27b and 27c of the sheath 20 are press fitted to a guide wire cock 23 and a liquid supply cock 24, respectively, via a pipe material (not shown) at the proximal end of the sheath 20. These lumens are structured such that its outside is fixed by a heat shrink tube 25 together with a press section 33 coupled with the above main body part 32. A water tight cock 28 (not shown) capable of inserting a guide wire for guiding a hollow medical device such as catheter is connected to this guide wire cock 23, a position of such guide wire is fixed, and is preferably structured to prevent back flow such as contrast medium while the guide wire is not used.

The sheath 20 is not limited to a tube structure having three lumens as described above. If there is provided a proper tube structure having one or more lumens, any sheath can be employed. In addition, although the outer diameter of the sheath 20 is structured to form the tip end portion 21 with its smaller diameter than the proximal end portion 22 as described above, the sheath may be formed in the same diameter from the tip end to the proximal end portion or may have the tapered shape at one portion along the longitudinal axis from the proximal portion to the tip end portion. Further, the knife wire 10 and the knife chip 11 can be fixed by proper methods such as plasma welding, blazing, soldering, or bonding with adhesive. Methods for fixing the sheath 20 to the knife 11 include: press-in fixing with a knife chip having its stepped shape; fixing with adhesive and/or friction; fixing via a plate material or the like; or fixing in which a part of the sheath is deformed. The fixing position may be at the tip end or proximal end of the tip end groove 26a without being limited to the shown position.

The sheath 20 may be connected to the guide wire cock 23 or the liquid supply cock 24, and the guide wire cock 23 may be connected to the water tight cock 28, by an appropriate method such as pressing or bonding (using adhesive or like). The heat shrink tube 25 may be one that has an inner surface coated with adhesive. A pipe (not shown) connects the cock 23 to the lumen 27b, and a pipe (not shown, either) connects the cock 24 to the lumen 27c, by means of bonding using adhesive, press-fitting, caulking or the like. It is preferable that illustrations or characters and the like be assigned to each of the cocks 23, 24, and 28 for clarity.

As shown in detail in FIG. 3 and FIG. 4, between grooves 26a and 26b, an exposed portion 13 of a knife wire 10 exposed to the external wall surface of the sheath 20 is overhung upwardly and laterally at a position proximal to the tip end groove 26a by means of the guide arm section 12. On the other hand, such guide arm section is not provided at a position proximal to the proximal end groove 26b, and thus, is introduced into the lumen 27a of the sheath 20 while a smooth curve is maintained. More precisely, the part 13 of the knife wire 10, which is exposed at the outer surface of the sheath 20, is bent at a position near the groove 26a, protruding from the plane 20a including the axes of the grooves 26a and 26b, the axis of the knife chip 11 and the axis of the sheath 20.

Figure 5A:
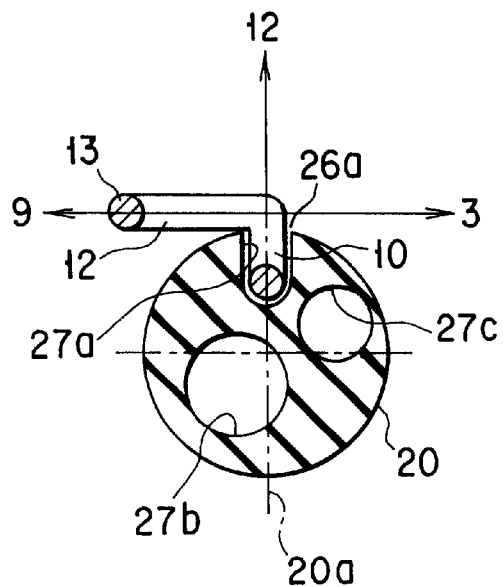
FIG. 5A and FIG. 5B show an exposed portion of the wire knife according to individual embodiments, each of the figures being a longitudinal cross section taken along the line A of FIG. 4.

FIG. 5A is a transverse cross section of the sheath 20, as viewed in the direction of arrow A shown in FIG. 4. Assume that the cross section is a clock dial and that the tip-end groove 26a extends in the direction of 12 o'clock. Then, the guide arm 12 is bent by 90° at the opening of the tip-end groove 26a and then extends in the direction of nine o'clock from the knife wire 10 provided in the lumen 27a. Further, after the guide arm section has been protruded from the external wall surface, it is further bent by substantial 90 degrees to be oriented in the substantial 9 o'clock direction. Therefore, the exposed portion 13 of the knife wire 10 is substantially disposed in the approximately 9 o'clock direction. On the other hand, at a position adjacent to the proximal end groove 26b, the knife wire 10 is oriented to the proximal end along the longitudinal axis direction of the sheath 20. The bending angle of the guide arm portion 12 of the knife wire 10 is not limited to the above value. It is possible to bend at an arbitrary angle within the range of 90 degrees±60 degrees with respect to the longitudinal axis of the sheath 20. In addition, for a position at which the knife wire 10 is disposed at the sheath 20, an arbitrary position such as 10 o'clock, 11 o'clock, 12 o'clock, and 3 o'clock other than the above can be selected.

(Operation)

In the case where EST is performed using the thus formed high-frequency knife, for example, the insert section of the sheath 20 through which the knife wire 10 is inserted is inserted into cavities trans-endoscopically. While the cavities are observed through endoscope, its tip end portion is inserted from a duodenal papilla to a bile duct positioned at the depth. A slider 31 is pulled to the right shown in FIG. 1B with respect to the main body 32, the tip end portion of the sheath 20 is bent, and the exposed portion 13 of the knife wire 10 exposed to the external wall surface is tensioned between grooves 26a and 26b, thereby forming a dissection portion. Thereafter, this dissection portion is brought into contact with the duodenal papilla portion, and a high-frequency current from the high-frequency power source is supplied to a conductive wire 10, thereby dissecting a sphincter.

In this manner, when the exposed portion 13 of the knife wire 10 is tensioned, thereby forming a dissection portion, the knife chip 11 orients the tip end portion to the proximal end of the sheath, and is fixed into the lumen 27a along the longitudinal axis. The guide arm section 12 is bent from this knife chip 11 to the longitudinal axis, and is protruded outwardly in a radial direction. When the slider 31 is pulled in the right direction shown in FIG. 1B, the outer end of the guide arm section 12 is pulled toward the proximal end portion via the exposed portion 13 of the knife wire 10 at the end portion of the sheath 20, and the tip end portion of the sheath 20 is bent. That is, the guide arm section 12 disposed in the tip end groove 26a of the sheath 20 is bent by 90 degrees with respect to the longitudinal axis toward the sheath 20 in the longitudinal central plane 20a of the sheath 20. Further, the guide arm section is bent by 90 degrees with respect to this longitudinal central plane 20a. At a position at which the exposed portion 13 is disposed at the sheath 20, the opening direction of the tip end groove 26a is oriented to the twelve o'clock direction, and the knife wire 10 is pulled to the nine o'clock direction at a position proximal to the tip end groove 26a. On the other hand, at a position adjacent to the proximal end groove 26b, the wire is pulled to the proximal end portion along the longitudinal axis of the sheath 20. Namely, when the slider 31 is pulled, the exposed portions 13 of the knife wire 10 are pulled in their different directions, respectively, at the tip end and proximal end of the sheath 20. Further, the guide arm section is bent by 90 degrees with respect to this longitudinal central plane 20a. At a position at which the exposed portion 13 is disposed at the sheath 20, the opening direction of the tip end groove 26a is oriented to the twelve o'clock direction, the knife wire 10 is pulled to the nine o'clock direction at a position proximal to the tip end groove 26a because of nine o'clock. On the other hand, at a position adjacent to the proximal end groove 26b, the wire is pulled to the proximal end portion along the longitudinal axis of the sheath 20. Namely, when the slider 31 is pulled, the exposed portions 13 of the knife wire 10 are pulled in their different directions, respectively, at the tip end and proximal end of the sheath 20.

(Advantageous Effect)

Therefore, in the high-frequency knife according to the present embodiment, the exposed portion 13 exposed to the external wall surface of the sheath 20 via two grooves 26a and 26b punched to be spaced from each other along the longitudinal axis at the dissection portion of the knife wire 10 performing dissecting in general EST, that is, at the external wall of the tip end portion of the sheath 20, is bent by 90 degrees with respect to the sheath 20 by means of the guide arm section 12 in the vicinity of the tip end groove 26a, and disposed in the nine o'clock direction. Therefore, the exposed portion is pulled out laterally of the longitudinal central plane of the sheath passing through the two grooves 26a and 26b and the fixing section 11. When the knife wire 10 is pulled, the knife wire is prone to be oriented in the nine o'clock to twelve o'clock direction spaced from the pancreas. This makes it unnecessary to perform a cumbersome operation that the surgeon changes an inconvenient orientation of the knife to a predetermined direction which has been performed by the surgeon when a conventional high-frequency knife is used. This makes it possible to perform EST by a smooth and simple operation. Furthermore, a complicated structure such as a direction control member employed for the conventional high-frequency knife is eliminated, whereby these effects can be achieved easily by an inexpensive high-frequency knife. At the same time, the knife wire 10 has the bent guide arm section 12, whereby the tip end of the knife chip 11 can be fixed to be oriented to the proximal end of the sheath 20, and the knife 11 is more difficult to be slipped off from the sheath 20 than the conventional knife wire.

Even using a combination other than the above, the bending angle and protrusion direction of the knife wire are changed, whereby the knife wire direction at the tip end position of the exposed portion of the knife wire can be controlled easily and inexpensively to an arbitrary orientation.

Figure 5B:
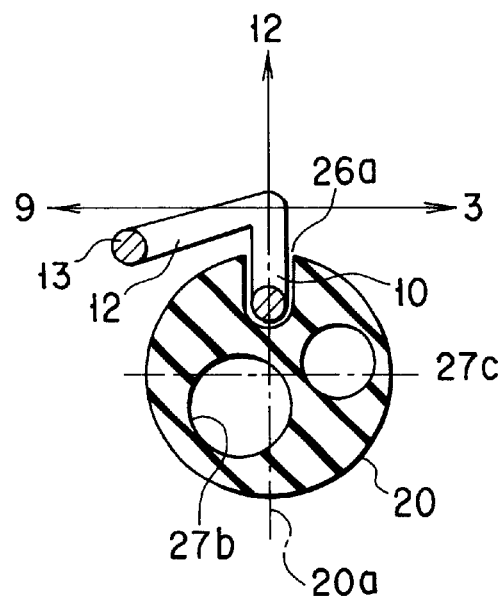

FIG. 5B shows an embodiment in which the bending angle of the knife wire 10 is thus changed. The knife wire 10 according to the present embodiment extends from the external wall surface to the twelve o'clock direction via the tip end groove 26a when the guide arm section 12 is bent by 90 degrees in the longitudinal central plane 20a. Further, after the knife wire has been extruded from the external wall surface of the sheath 20 by a predetermined distance, the wire is bent in the six o'clock to nine o'clock direction in a plane passing through the tip end groove 26a and perpendicular to the longitudinal central plane 20a. A distance in which this guide arm section 12 extends from the lumen 27a to the twelve o'clock direction is longer than that shown in FIG. 5A.

At the exposed portion 13 of the knife wire 10 according to the present embodiment, the transverse cross section taken as the aforementioned character plate can be protruded in an arbitrary direction from the three o'clock to nine o'clock direction via the six o'clock direction near the tip end groove 26a. The other structure, operation, and advantageous effect is similar to those of the aforementioned illustrative embodiment.

Figure 7A:
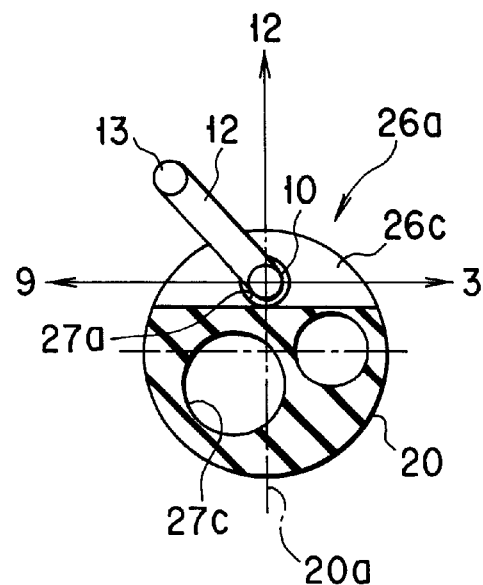
FIG. 7A and FIG. 7B each are sectional views similar to FIG. 4, each of the figures showing a sheath according to another embodiment when their dispositions are changed.
Figure 7B:
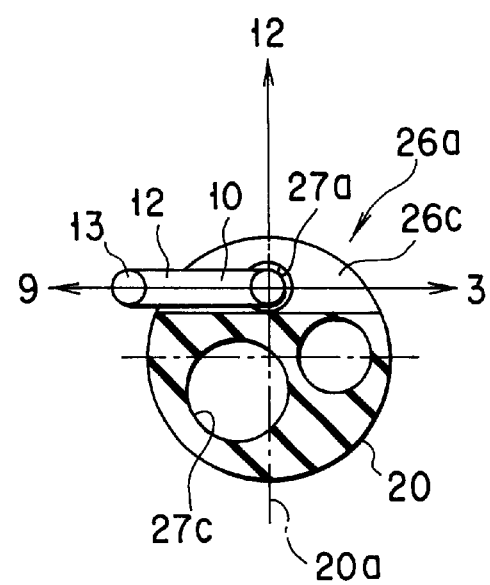
Figure 6:
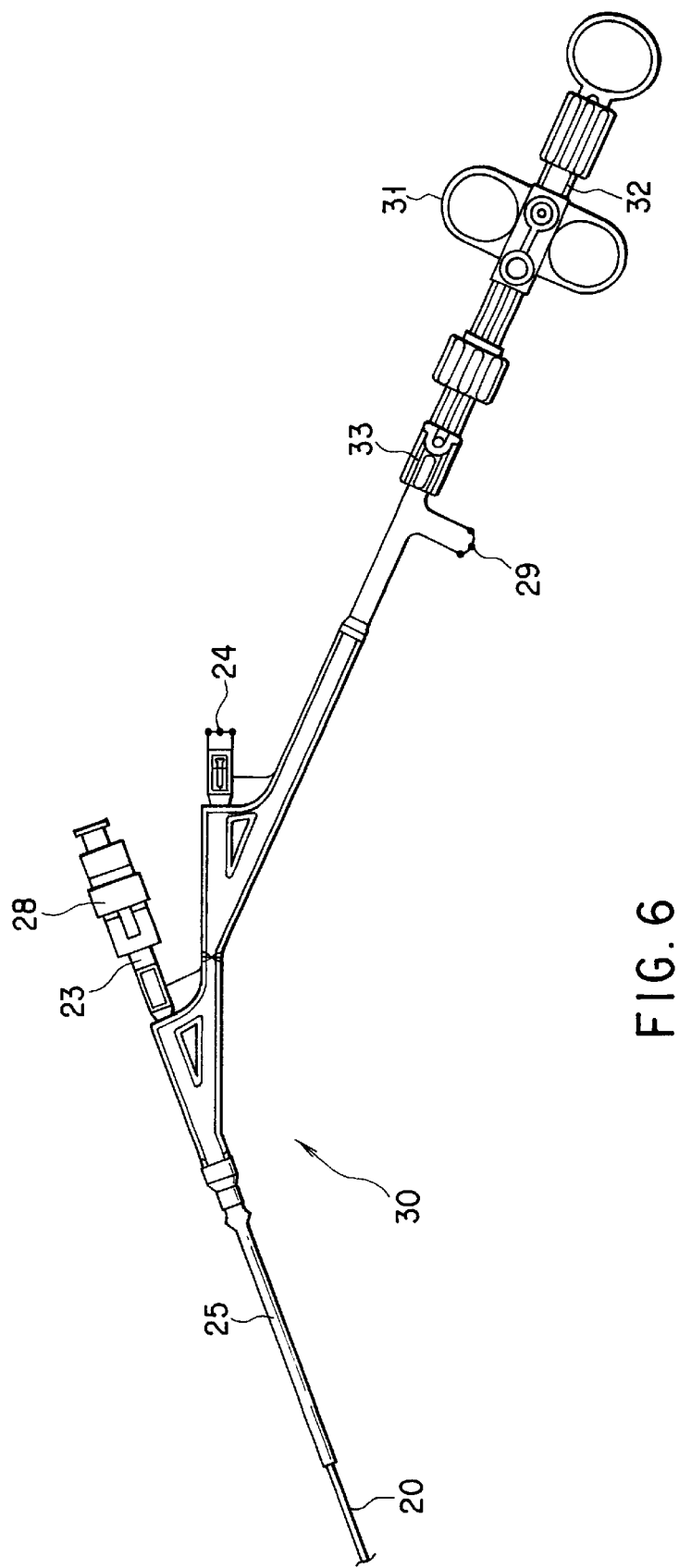
FIG. 6 is an illustrative view showing an operating section of the high-frequency knife according to another embodiment.

FIG. 6, FIG. 7A and FIG. 7B show a high-frequency knife according to another embodiment. The high-frequency knife according to this embodiment is basically similar to that of the above embodiment. Therefore, elements different from those of the above embodiment will be described. Like elements are designated by like reference numerals. A detailed description of these elements will be omitted here.

In this illustrative embodiment, a guide wire cock 23, a liquid supply cock 24, and a water-tight cock 28 are provided at the main body part 32 of the operating section 30, and this main body part 32 is externally fixed by the heat shrink tube 25 together with the sheath 20. In the present embodiment, a wash cock 29 is further provided at the main body part 32, facilitating wash after use.

Further, as shown in FIG. 7A and 7B, the tip end groove 26a in the present embodiment has a semi-circular shape when it is seen from the transverse cross section of the sheath 20. The lumen 27a opens around its full periphery in the proximal end face 26c of the groove 26a. In addition, the guide arm section 12 of the knife wire 10 is not bent in a plane parallel to this transverse cross section. Therefore, the guide arm section 12 is formed in linear shape in which the knife chip 11 and the exposed portion 13 are linked with each other by the shortest distance. As shown in FIG. 7A and FIG. 7B, when a transverse cross section passing through the groove 26a is taken as a clock character plate, the guide arm section 12 and the exposed portion 13 can be disposed at an intermediate position between nine o'clock direction and 12 o'clock direction as shown in FIG. 7A or at an arbitrary position as required such as nine o'clock position shown in FIG. 7B. The disposition of this guide arm section 12 and the exposed portion 13 can be maintained by fixing the knife chip 11 at a desired position in the lumen 27a so as not to be rotational.

In the present embodiment, an effect similar to that of the aforementioned embodiment can be achieved, and the guide arm section 12 can be formed in linear shape. Thus, the knife wire 10 can be structured more simply. Further, the tip end groove 26a has a semi-circular shape when it is seen from the transverse cross section of the sheath, and the disposition of the exposed portion 13 can be easily set.

As in the present embodiment, when the transverse cross section of the sheath 20 passing through this groove 26a and seen from the proximal end is taken as a clock character board while the groove 26a is set upwardly, in the case where the upper side of the longitudinal central plane 20a of the sheath 20 passing through the center axis of the sheath 20 and the knife chip 11 is defined as 12 o'clock, the aforementioned tip end groove 26a may be opened in the range of 90 degrees counterclockwise, for example, from the twelve o'clock direction along the aforementioned longitudinal central plane 20a in addition to the semi-circular shape from nine o'clock to the three o'clock through the 12 o'clock or may be opened in the range of 45 degrees±30 degrees. Further, with respect to the protrusion direction from the sheath 20 of the guide arm section 12, after the guide arm section has been protruded in the 12 o'clock direction as shown in FIGS. 5A and 5B, the guide arm may be further protruded in the nine o'clock direction. In addition, from the aforementioned opening, the guide arm section may be protruded at a position between nine o'clock and twelve o'clock as shown in FIG. 7A, may be protruded at a position of nine o'clock as shown in FIG. 7B, or may be protruded in a direction between nine o'clock and eleven o'clock. In particular, in the case of the substantially circular shape groove 26a as shown in FIG. 7A and FIG. 7B, at the exposed portion 13 of the knife wire 10, the transverse cross section taken as the aforementioned character plate can be protruded near the tip end groove 26a in an arbitrary direction between nine o'clock and three o'clock through twelve o'clock.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscopic high-frequency knife comprising:
   a flexible sheath adapted to be inserted into a body, said sheath having an external surface;
   a front-end slit and a rear-end slit arranged in line in the external surface of the sheath where a first imaginary plane including a central axis of the sheath intersects the external surface of the sheath;
   a conductive wire having an arm section protruding through the front-end slit, an incision section which is arranged continuous with the arm section, and an operation section which is continuous with the incision section and inserted through the rear-end slit into the sheath and which operates the incision section;
   wherein the arm section has a predetermined length and extends in a direction intersecting the first imaginary plane.

2. A high-frequency knife according to claim 1, wherein the incision section does not have a bend in a vicinity of the rear-end slit, and is introduced into the rear-end slit in a smooth curve shape.

3. A high-frequency knife according to claim 1, wherein the arm section is disposed at an angle position between nine o'clock and three o'clock via twelve o'clock when an imaginary clock face is superimposed on the arm section and an opening direction of the front-end slit is positioned at twelve o'clock when the arm section is seen from a rear end of the sheath.

4. A high-frequency knife according to claim 1, wherein the arm section has an angle ranging from 90 degrees±60 degrees with respect to the central axis of the sheath.

5. A high-frequency knife according to claim 3, wherein the arm section is disposed at an angle position between nine o'clock and twelve o'clock when the imaginary clock face is superimposed on the arm section and the opening direction of the front-end slit is positioned at twelve o'clock when the arm section is seen from a rear end of the sheath.

6. A high-frequency knife according to claim 3, wherein the arm section is disposed at an angle position between nine o'clock and eleven o'clock when the imaginary clock face is superimposed on the arm section and the opening direction of the front-end slit is positioned at twelve o'clock when the arm section is seen from a rear end of the sheath.

7. A high-frequency knife according to claim 1, wherein the arm section is disposed in a second imaginary plane crossing the first imaginary plane, and has a bend at a predetermined angle in the second imaginary plane.

8. A high-frequency knife according to claim 7, wherein the predetermined angle is 90 degrees or less.

9. A high-frequency knife according to claim 1, wherein the front-end slit is semicircular as viewed from a proximal end thereof and extends at an angle of 90 degrees measured from the first imaginary plane in a counterclockwise direction, and said first imaginary plane extends in a direction of 12 o'clock when an imaginary clock face is superimposed on a transverse cross section of the sheath.

10. A high-frequency knife according to claim 1, wherein the front-end slit is semicircular as viewed in an axial direction of the sheath from a proximal end thereof and extends at an angle of 45°±30° measured from the first imaginary plane in a counterclockwise direction, and said first imaginary plane extends in a direction of 12 o'clock when an imaginary clock face is superimposed on a transverse cross section of the sheath.

* * * * *